United States Patent [19]
Wekhof

[11] Patent Number: 5,144,146
[45] Date of Patent: Sep. 1, 1992

[54] METHOD FOR DESTRUCTION OF TOXIC SUBSTANCES WITH ULTRAVIOLET RADIATION

[75] Inventor: Alexander Wekhof, Emeryville, Calif.

[73] Assignee: Ultraviolet Energy Generators, Inc., Berkeley, Calif.

[21] Appl. No.: 684,458

[22] Filed: Apr. 11, 1991

Related U.S. Application Data

[63] Continuation-in-part of Ser. No. 549,506, Jul. 6, 1990, abandoned.

[51] Int. Cl.$^5$ .................................................. A61L 2/10
[52] U.S. Cl. ................................ 250/492.1; 422/24; 210/748
[58] Field of Search ............... 250/492.1, 455.1, 436.1; 422/24; 99/451; 210/748; 426/248

[56] References Cited

U.S. PATENT DOCUMENTS

| | | |
|---|---|---|
| 3,456,107 | 7/1969 | Robertson . |
| 3,911,318 | 10/1975 | Spero et al. . |
| 3,977,952 | 8/1976 | Knoevenagel et al. . |
| 3,978,341 | 8/1976 | Hoell . |
| 4,013,552 | 3/1977 | Kreuter . |
| 4,141,830 | 2/1979 | Last . |
| 4,214,962 | 7/1980 | Pincon . |
| 4,309,388 | 1/1982 | Tenney et al. . |
| 4,336,223 | 6/1982 | Hillman . |
| 4,427,636 | 1/1984 | Obenshain . |
| 4,438,337 | 3/1984 | Forrat . |
| 4,448,750 | 5/1984 | Fuesting . |
| 4,464,336 | 8/1984 | Hiramoto ........................ 422/24 |
| 4,504,445 | 3/1985 | Walz . |
| 4,526,034 | 7/1985 | Campbell et al. . |
| 4,762,613 | 8/1988 | Snowball . |
| 4,769,131 | 9/1988 | Noll et al. . |
| 4,798,702 | 1/1989 | Tucker . |
| 4,871,559 | 10/1989 | Dunn et al. ........................ 422/24 |
| 4,880,512 | 11/1989 | Cornelius et al. ............... 204/157.61 |
| 4,952,812 | 8/1990 | Miripol et al. .................... 250/492.1 |

OTHER PUBLICATIONS

Pub. Xenon Corporation product literature, "RC-500 High Performance Pulsed UV Curing System with Continuous Duty Capability".

*Primary Examiner*—Jack I. Berman
*Attorney, Agent, or Firm*—Townsend and Townsend

[57] ABSTRACT

A method for destruction of toxic compounds through direct ultraviolet irradiation. Continuum UV radiation from the deep region of the spectrum is applied to the target medium in pulsed fashion with a specified range of power ratios and average power. Enhanced destruction of undesirable toxins is achieved when the ratio of rms power to average power falls in characteristic range of 50:1 to 200:1; the ratio of peak power to average power falls in the characteristic range of 1000:1 to 10,000:1; and the average power density is maintained at least at a value of about 0.5 Watt/cm$^2$ within the carrier medium.

4 Claims, 3 Drawing Sheets

METHOD FOR DESTRUCTION OF TOXIC SUBSTANCES WITH ULTRAVIOLET RADIATION

This is a continuation-in-part of application Ser. No. 07/549,506, filed Jul. 6, 1990, now abandoned.

BACKGROUND OF THE INVENTION

The present invention relates to the destruction of toxic substances such as organic compounds and microbial species in the process of purification or disinfection of aqueous and other environments.

Various undesirable compounds, such as heavy organic molecular compounds and microbial species, are often carried in waste water or other effluents, soils or other matrix environments, in which they may prove toxic in subsequent uses of the carrier material. One known process for sterilizing or disinfecting the carriers of these compounds is through irradiation with ultraviolet (UV) radiation. Most chemical bonds in organic toxins are broken under the action of the ultraviolet radiation through photodissociation. A particular substance will have a characteristic photodissociation curve associated with it specifying the energies of UV radiation for which the particular substance will undergo photodissociation. For effective photodissociation it is necessary that the UV radiation have the particular energy or energies which fall within the photodissociation curve of the substance of interest. For most organic toxins of interest here the photodissociation curves are greatest (indicating the greatest likelihood of dissociation) in the range of 175 to 300 nanometers (nm).

Most dissociation curves of interest have an effective range which can include many discrete UV emission energies (so-called emission "lines"). For effective destruction of the undesirable compounds it is not enough that the UV energies fall in the applicable range. Another necessary condition is that the radiation have a sufficient intensity. The necessary intensity depends on the photodissociation cross sections for the undesirable compounds and their concentrations in the carrier medium.

There is also a problem in effective destruction of toxic compounds in that the photodissociation process for a given compound may produce by-products which are themselves toxic and which must undergo further photodissociation until non-toxic end-products result. In other words a cascade of consequent UV photodissociation actions has to be applied to the original toxins and to the possibly toxic byproducts of the UV actions until the final byproducts are reduced to safe substances.

Typical UV sources generate only a relatively few intense UV emission lines falling in this energy range. These relatively few intense lines do not generally fall within the peak absorption range for all of the toxic compounds and their photodissociation byproducts occurring in a typical specimen.

Direct UV destruction of toxic compounds has not been employed in the prior art, which instead has relied on UV excitation of known intermediate additives such as ozone or peroxides.

SUMMARY OF THE INVENTION

The present invention provides a method for breaking down toxic compounds of the above sort into their final non-toxic end-products through direct ultraviolet irradiation. The invention achieves this result by applying sufficiently intense UV radiation from the deep region of the UV spectrum in a sufficiently broad band to form an effective continuum and thereby overlap with the absorption curves for essentially any of the toxins of interest and of their toxic byproducts (if any) from such UV photodissociation. More particularly, it has been found that effective destruction of toxins with concentrations ranging from 200 parts per million (ppm) to 10 parts per billion (ppb) can be achieved by delivering the deep UV radiation to the target medium in pulsed fashion where the root-mean-square (rms) and peak power delivered by the UV source are related to the average power by characteristic ratios, while the average power density is at least a minimum characteristic value. The precise values of the characteristic ratios and power densities that optimize the destruction of the target toxins depends upon the concentrations and the carrier medium of the toxins. Nevertheless, it has been found that the surprisingly effective destruction achieved by the invention will generally be attained when the ratio of rms power to average power falls in the characteristic range of 10:1 to 100:1; the ratio of peak power to average power falls in the characteristic range of 1000:1 to 10,000:1; and the UV average power density is maintained at least at a value of about 0.1 Watt/cm$^2$ within the carrier medium. The characteristic profile of the UV radiation provided according to the invention is such that it can be achieved within the bounds of a practical instrument.

Other features and advantages of the invention will be described below or will be apparent to those skilled in the, art from the following description and accompanying drawings.

DETAILED DESCRIPTION OF ILLUSTRATIVE EMBODIMENTS

The present invention calls for subjecting the toxic species desired to be destroyed to ultraviolet radiation under special conditions, which are indicated below. By way of illustration the invention is described here as applied to the purification of waste water. Those skilled in the art will appreciate from the present disclosure, however, that the invention may be applied to destroy undesirable species in a variety of other environments as well.

Apparatus for subjecting the water under treatment to ultraviolet radiation is well known to persons skilled in the art and need not be described here in any detail. For simplicity, therefore, the apparatus is illustrated only diagrammatically in FIG. 1. For treatment of materials other than waste water it will be necessary of course to employ apparatus suitable for the particular material under treatment to expose the material to a source of UV radiation.

Figure 1:
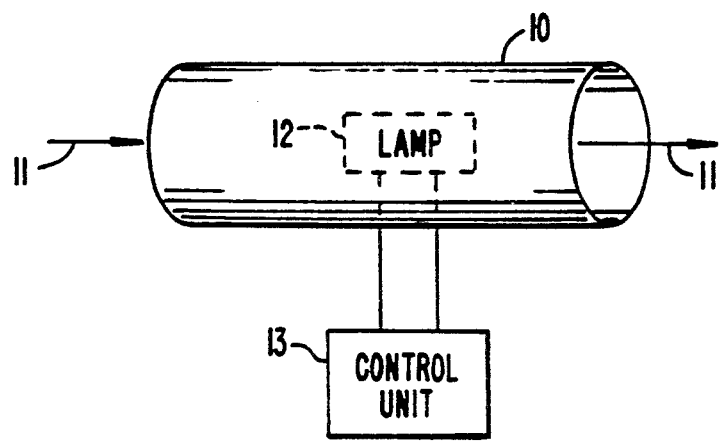
FIG. 1 is a diagrammatic view of apparatus for practicing the invention.
Figure 2:
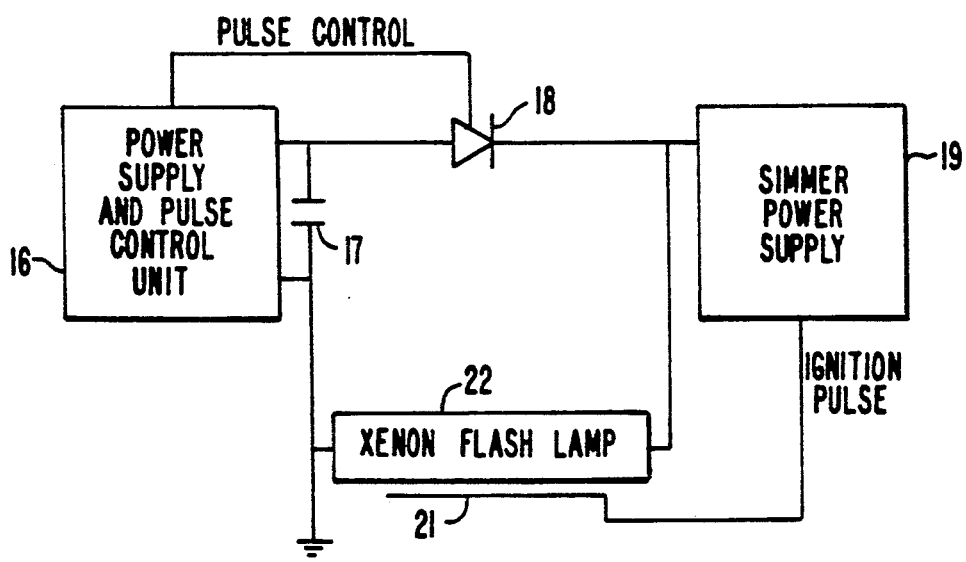
FIG. 2 is a block schematic diagram of the control unit and lamp of FIG. 1.

FIG. 1 shows a processing chamber 10 through which the water under treatment flows in the direction indicated by the arrows 11. Embedded within chamber 10 is a source 12 of UV radiation. Although illustrated as embedded within chamber 10, the UV source 12 may, of course, also be situated outside the chamber and irradiate the water under treatment through quartz windows transparent to UV radiation. UV source 12 is driven by control unit 13.

It has been found that highly effective purification can be achieved for a wide range of toxins if the UV source is caused to provide an irradiating beam, operated in a pulsed mode, and having a characteristic frequency profile as well as a characteristic power profile. The frequency spectrum of the individual pulses includes UV radiation in a band in the wavelength range of 175 to 360 nm. The band may comprise a continuous spectrum or at least a band of discrete emission lines of sufficiently high density approximating a continuous spectrum. The process as described is advantageous in part because the UV radiation is delivered in an intense continuum which overlaps the absorption curves of most toxins. Thus, the destructive power of the process is not limited to a particular toxic substance arising in a particular application, but is effective against a broad range of substances and their toxic byproducts generated when the primary toxin is broken down by a cascade of consequent photolytic actions of the pulsing UV continuum.

Known methods in the past have avoided the use of a continuous spectrum, instead employing UV radiation at specific available frequencies, such as the frequencies of the basic mercury lines or other available lines in metal halide lamps. Furthermore, radiation at the frequencies of these lines are typically used to activate intermediate agents such as ozone or peroxide. These methods lack sufficient power at the characteristic frequencies for breaking down the toxins directly.

It has been discovered in the present invention that the above limitations may be overcome and a great enhancement in the destructive capability of the UV radiation may be achieved by adjusting the peak power, the rms power, and the pulse rate and average power at which the radiation is delivered to the medium while providing at least a minimum power density level for the destruction of the toxic concentrations of interest in any given example. The precise values of these parameters in any given case depends upon, and can be calculated from, the photodissociation cross sections and the concentrations of the target toxins. The techniques for performing such calculations are well known in the field of UV absorption spectroscopy and the necessary cross sections, for the most part, have been measured and may be found in the available technical literature. Nevertheless, such calculations may be tedious, and as a practical matter, it will be simpler to determine the optimal values of the parameters in any given case empirically. For example, as a baseline for comparison a sample under treatment may be continuously exposed to radiation from a mercury lamp for, say, five minutes, and the resulting reduction in concentration of the toxic substances measured. An equivalent sample may then be exposed to a pulsed beam at the same average power level and the resulting destruction of toxins again measured. The peak power and rms power are then adjusted, e.g., by adjusting the current and rise time in the UV lamp, and the variation in concentrations noted. Then the pulse repetition rate may be adjusted and the change noted. In this manner the approximate optimum values of the system parameters may be determined empirically with a relatively few iterations.

While the precise values optimizing performance will generally depend on the specific target medium and toxins, nevertheless, it has been found that the surprisingly effective destruction achieved by the present invention will generally be attained when the ratio of rms power to average power falls in the characteristic range of 10:1 to 100:1; the ratio of peak power to average power falls in the characteristic range of 1000:1 to 10,000:1; and the average power density is maintained at least at a value of about 0.1 Watt/$cm^2$ within the carrier medium while the UV source is pulsed at a repetition rate in the range of 5 to 100 Hertz (Hz). These ratios assure that the processes by which the bonds in the toxins are broken are far more prevalent than the competing reverse processes. The peak power may of course be greater than indicated in the above ratio and a greater average power than indicated above will, of course, be even more beneficial.

For example, an average power, rms power, and peak power in the relative proportions of:

average power:rms power:peak power=1:20:2000 has been found to be effective for concentrations, of volatile and semi-volatile toxins in the range between 100,000 and 50 ppb. For oil and grease at a concentration on the order of 10,000 ppb the effective proportions were found to be 1:10:1000.

In this way, a variety of toxins may be effectively treated without having to tune or select the UV source specifically to the toxins of interest and consequently without even having to know in advance the composition of toxins present. If, however, the combination of toxic substances present in the sample under treatment should be known in advance, then the absorption curves of the individual substances may be determined through known UV absorption spectroscopy techniques and the source parameters adjusted to match the principal portion of the absorption curves with the principal portion of the continuum from the UV. For example, if the toxins present are known to have absorption curves in the limited range of, e.g., 200 to 240 nm, then the process efficiency may be enhanced by tailoring the output of the UV source to this range, i.e., by adjusting the source parameters to increase the output in this range and to minimize the output outside of this range.

The pulse rate of the source may also be adjusted according to the toxin concentration and sample flow rate. For example, for contaminated water passing through the system at a flow rate of 80 gallons per minute (gal/min), the pulse rate may be set at 40 pulses per second. If the flow rate should slow to 64 gal/min, then the pulse rate may follow the change in flow rate and be slowed proportionately to 32 pulses per second.

With reference now to FIGS. 1 and 2, the process according to the present invention may be practiced with a UV source 12 provided by a xenon flash lamp having a high quality quartz (suprasil) envelope. The lamp may be driven with the power supply and switching circuit arrangement shown in the block schematic diagram of FIG. 2, which includes a power supply and pulse control unit 16, charging capacitor 17, silicon controlled rectifier (SCR) 18, simmer power supply 19, ignition wire 21 and xenon flash lamp 22. Charging capacitor 17 typically has a capacitance on the order of 4 microfarads and power supply 16 provides a charging voltage in the range of 2 to 5 kV. The network operates to produce a small (2 to 3 Ampere) DC current through lamp 22 (so-called simmer current). The voltage across lamp 22 corresponding to this DC current will typically be 70 to 200 Volts once the simmer current is established. To establish the simmer current, an initial voltage of about 1 kV DC is applied to the lamp and the lamp is ignited with a high voltage spark through ignition wire 21. As soon as the simmer current is established, SCR 18 can be opened periodically to discharge the capacitor into lamp 22. With this arrangement and a lamp having a bore diameter of 6 mm, a peak current of 1,500 Amperes can be reached with a rise time of about 7 microseconds. In general, with a xenon flash lamp a pulsed peak current density J of 4 to 8 kiloamperes per square centimeter ($kA/cm^2$) and a rate of rise $dJ/dt$ of 200 to 500 amperes per square centimeter per microsecond ($A/cm^2$-μsec) may be achieved.

Figure 3A:
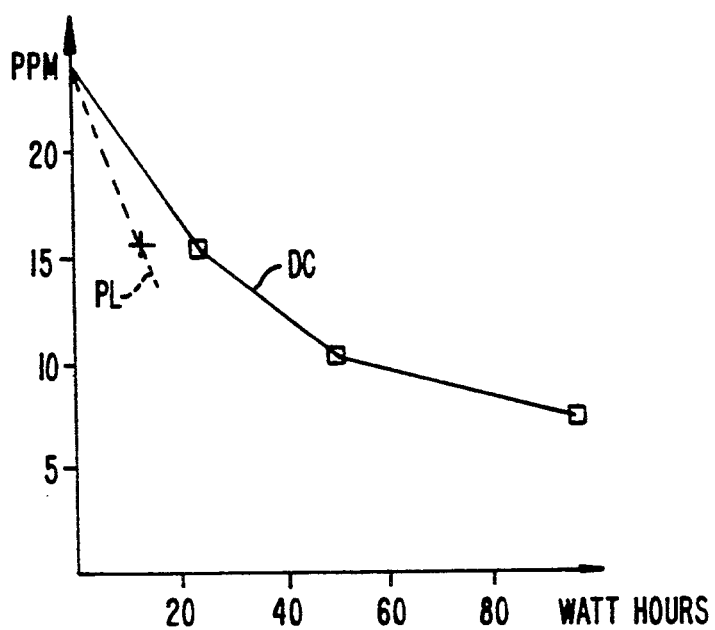
FIGS. 3A and 3B show comparative test results for the process according to the invention.
Figure 3B:
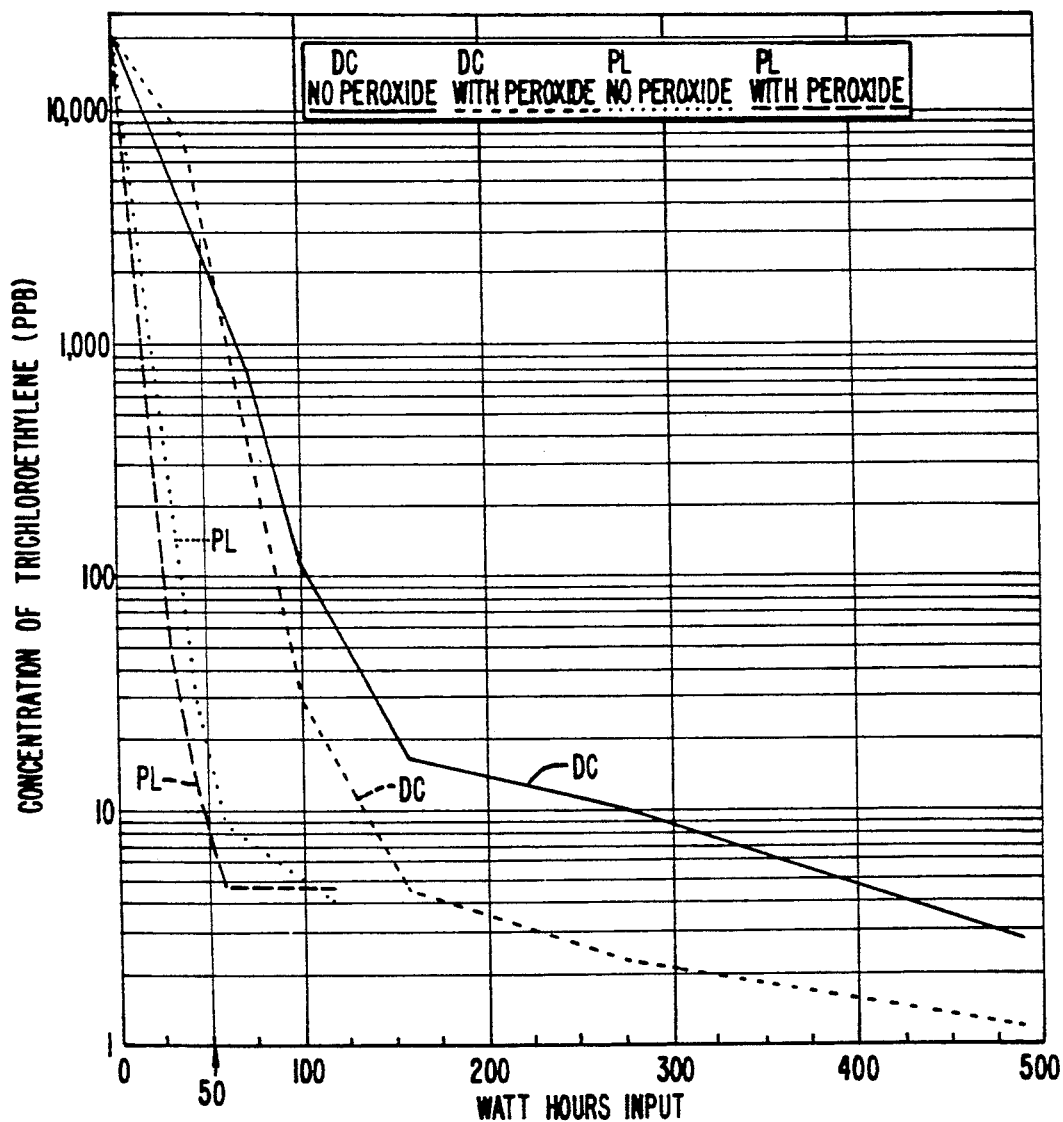

The process described herein has been demonstrated to break down major organic toxins directly into simple, non-toxic end-products significantly more effectively than could be achieved with a standard DC mercury lamp with the same average electrical power input. FIGS. 3A and 3B show the results of sample test runs. The test data were achieved using a xenon flash lamp driven under the conditions described above.

FIG. 3A shows the photolytic destruction of a sample of emulsified oil using the pulsed continuum UV radiation with power ratios as described above. The curve labeled DC shows the reduction of oil contaminants in the sample achieved with a lamp run continuously in the conventional direct current mode. The curve labeled PL shows the reduction in the same sample using the "pulsed light" mode according to the present invention.

FIG. 3B shows a similar test performed with a sample contaminated by trichloroethylene. The curves labeled DC show the destruction of the contaminant by UV irradiation using a medium pressure mercury lamp without the benefit of the present invention. In one DC curve the sample is merely irradiated. In the other DC curve peroxide has also been added to the sample. The curves labeled PL show the improvement achieved in both cases by means of the present invention. The PL curves were generated with power ratios of average:rms:peak = 1:20:2000;

the average flux density over the sample was $P_{Av} = 0.40$ $W/cm^2$ in the UV region. Note that at 50 Watt-hours of applied electrical energy, the destruction is about 100 times more effective than the action with the mercury lamp.

The above provides a full and complete disclosure of illustrative embodiments of the present invention. Given the benefit of this disclosure, various alternate embodiments, modifications, and equivalents will occur to those skilled in the art. For example, a variety of arrangements may be employed to irradiate the material under treatment, and a variety of lamps and power supply designs may be configured to provide the pulse, frequency, and power profiles called for by the invention. The process of the present invention is believed to achieve its destructive results principally through direct photodissociation of the target toxins into safe final byproducts by a cascade of photolytic actions of a pulsing UV continum applied to initial toxins and their toxic byproducts (if any). This cascade process of consequent photolytic actions is effectively sustained due to the fact that the pulsing UV continuum with an established range of average, rms and peak ratios has the most effective photolytic action on any of the original toxins and on any of their photolytic byproducts if the latter are also toxic. The process can be terminated when all photolytic byproducts are reduced to safe substances. It will thus be appreciated by those skilled in the art that the process will be applicable not only to toxins in aqueous solution, but also to toxins in any environment in which the toxins are free to undergo direct photodissociation. Accordingly, the invention is not intended to be limited only to the specific examples and embodiments disclosed herein, but is defined by the appended claims.

What is claimed is:

1. A process for the destruction of toxic substances in a medium by means of ultraviolet radiation in which the medium is subjected to a band of ultraviolet radiation of high spectral density, said band lying within the wavelength range of 175 to 360 nanometers, said ultraviolet radiation being pulsed at a pulse repetition rate of at least about 5 Hertz, in which the ratio of root-mean-square power to average power of said ultraviolet radiation lies in the range of 10:1 to 100:1, and the ratio of peak power to average power delivered by said ultraviolet radiation lies in the range of 1,000:1 to 10,000:1, said ultraviolet radiation having an average power density of at least about 0.1 Watt/centimeter$^2$.

2. The process of claim 1 wherein said band of ultraviolet radiation of high spectral density is provided by a continuous band of ultraviolet frequencies.

3. The process of claim 1 wherein said band of ultraviolet radiation of high spectral density is provided by a dense band of discrete ultraviolet emission lines.

4. A process for the destruction of toxic substances by photodissociation comprising the steps of:

providing an extended spectral band of ultraviolet radiation lying within the range of 175 to 360 nanometers;

pulsing the ultraviolet radiation at a pulse repetition rate of at least about 5 Hertz, the pulsed extended spectral band of ultraviolet radiation having a characteristic rms power ratio of rms power to average power, a characteristic peak power ratio of peak power to average power, and a characteristic average power density; and adjusting said pulse repetition rate, said rms power ratio, said peak power ratio, and said average power density relative to one another to maximize destruction of said toxic substances and toxic byproducts thereof.

* * * * *